United States Patent
Germain et al.

(10) Patent No.: US 10,595,889 B2
(45) Date of Patent: Mar. 24, 2020

(54) ARTHROSCOPIC DEVICES AND METHODS

(71) Applicant: RELIGN Corporation, Cupertino, CA (US)

(72) Inventors: Aaron Germain, San Jose, CA (US); Jeffrey Norton, Emerald Hills, CA (US); Salvatore G. Mangano, San Jose, CA (US); Michael D. Walker, San Francisco, CA (US); Steffan Benamou, Morgan Hill, CA (US)

(73) Assignee: RELIGN Corporation, Campbell, CA (US)

( * ) Notice: Subject to any disclaimer, the term of this patent is extended or adjusted under 35 U.S.C. 154(b) by 436 days.

(21) Appl. No.: 15/483,940

(22) Filed: Apr. 10, 2017

(65) Prior Publication Data

US 2017/0290602 A1    Oct. 12, 2017

Related U.S. Application Data

(60) Provisional application No. 62/325,224, filed on Apr. 20, 2016, provisional application No. 62/325,326,
(Continued)

(51) Int. Cl.
*A61B 17/32* (2006.01)
*A61B 17/00* (2006.01)
(Continued)

(52) U.S. Cl.
CPC .. *A61B 17/320016* (2013.01); *A61B 17/1608* (2013.01); *A61B 34/74* (2016.02);
(Continued)

(58) Field of Classification Search
CPC ........ A61B 17/320016; A61B 18/1482; A61B 18/1445; A61B 2017/00398; A61B 34/77; A61B 2017/320028; A61B 2018/00601
See application file for complete search history.

(56) References Cited

U.S. PATENT DOCUMENTS

| 2,513,564 A | 7/1950 | Ingwersen |
| 2,514,545 A | 7/1950 | Ingwersen |

(Continued)

FOREIGN PATENT DOCUMENTS

| DE | 102005059864 A1 | 6/2007 |
| EP | 1034747 A1 | 9/2000 |

(Continued)

OTHER PUBLICATIONS

European Search Report dated Nov. 2, 2009 for European Patent Application No. EP01967968.7.
(Continued)

*Primary Examiner* — Jocelyn D. Ram
(74) *Attorney, Agent, or Firm* — Wilson Sonsini Goodrich & Rosati

(57) ABSTRACT

Arthroscopic cutters are used for resecting tissues, such as meniscal tissues, in meniscectomies or other arthroscopic procedures. The arthroscopic cutters have a shaft assembly with openable-closeable jaws at a working end of the shaft. A handpiece having a motor drive may be detachably coupled to a hub on a hub end of the handpiece. When the shaft is coupled to the handpiece, the motor drive will couple to the jaw structure to open and close the jaw structure to cut meniscal and other tissues.

34 Claims, 9 Drawing Sheets

Related U.S. Application Data filed on Apr. 20, 2016, provisional application No. 62/321,114, filed on Apr. 11, 2016.

(51) Int. Cl.
*A61B 18/00* (2006.01)
*A61B 18/14* (2006.01)
*A61B 17/16* (2006.01)
*A61B 34/00* (2016.01)

(52) U.S. Cl.
CPC ....... *A61B 18/1445* (2013.01); *A61B 18/1482* (2013.01); *A61B 2017/0046* (2013.01); *A61B 2017/00137* (2013.01); *A61B 2017/00199* (2013.01); *A61B 2017/00398* (2013.01); *A61B 2017/00473* (2013.01); *A61B 2017/320028* (2013.01); *A61B 2018/00315* (2013.01); *A61B 2018/00565* (2013.01); *A61B 2018/00601* (2013.01); *A61B 2034/742* (2016.02); *A61B 2217/005* (2013.01); *A61B 2218/007* (2013.01)

(56) References Cited

U.S. PATENT DOCUMENTS

| | | | |
|---|---|---|---|
| 2,625,625 A | 1/1953 | Ingwersen | |
| 2,689,895 A | 9/1954 | Ingwersen | |
| 3,611,023 A | 10/1971 | Souza, Jr. et al. | |
| 3,838,242 A | 9/1974 | Goucher | |
| 3,848,211 A | 11/1974 | Russell | |
| 3,868,614 A | 2/1975 | Riendeau | |
| 3,899,829 A * | 8/1975 | Storm | A61B 17/32 30/228 |
| 3,903,891 A | 9/1975 | Brayshaw | |
| 4,060,088 A | 11/1977 | Morrison, Jr. et al. | |
| 4,272,687 A | 6/1981 | Borkan | |
| 4,781,175 A | 11/1988 | McGreevy et al. | |
| 4,895,146 A | 1/1990 | Draenert | |
| 4,936,842 A | 6/1990 | D'Amelio et al. | |
| 4,977,346 A | 12/1990 | Gibson et al. | |
| 5,012,495 A | 4/1991 | Munroe et al. | |
| 5,122,138 A | 6/1992 | Manwaring | |
| 5,207,675 A | 5/1993 | Canady | |
| 5,256,138 A | 10/1993 | Burek et al. | |
| 5,281,217 A | 1/1994 | Edwards et al. | |
| 5,433,721 A * | 7/1995 | Hooven | A61B 17/068 227/175.1 |
| 5,449,356 A | 9/1995 | Walbrink et al. | |
| 5,490,854 A | 2/1996 | Fisher et al. | |
| 5,520,634 A * | 5/1996 | Fox | A61B 17/32002 604/22 |
| 5,641,251 A | 6/1997 | Leins et al. | |
| 5,669,907 A | 9/1997 | Platt, Jr. et al. | |
| 5,683,366 A | 11/1997 | Eggers et al. | |
| 5,720,745 A | 2/1998 | Farin et al. | |
| 5,759,185 A | 6/1998 | Grinberg | |
| 5,766,195 A | 6/1998 | Nobles | |
| 5,776,092 A | 7/1998 | Farin et al. | |
| 5,810,809 A | 9/1998 | Rydell | |
| 5,823,971 A | 10/1998 | Robinson et al. | |
| 5,839,897 A | 11/1998 | Bordes | |
| 5,849,010 A | 12/1998 | Wurzer et al. | |
| 5,857,995 A | 1/1999 | Thomas et al. | |
| 5,873,855 A | 2/1999 | Eggers et al. | |
| 5,888,198 A | 3/1999 | Eggers et al. | |
| 5,891,095 A | 4/1999 | Eggers et al. | |
| 5,904,681 A | 5/1999 | West, Jr. | |
| 5,913,867 A | 6/1999 | Dion | |
| 5,957,884 A | 9/1999 | Hooven | |
| 5,964,752 A | 10/1999 | Stone | |
| 5,989,248 A | 11/1999 | Tu et al. | |
| 6,007,553 A | 12/1999 | Hellenkamp et al. | |
| 6,013,075 A | 1/2000 | Avramenko et al. | |
| 6,013,076 A | 1/2000 | Goble et al. | |
| 6,024,733 A | 2/2000 | Eggers et al. | |
| 6,032,674 A | 3/2000 | Eggers et al. | |
| 6,039,736 A | 3/2000 | Platt, Jr. | |
| 6,056,747 A | 5/2000 | Saadat et al. | |
| 6,066,134 A | 5/2000 | Eggers et al. | |
| 6,099,523 A | 8/2000 | Kim et al. | |
| 6,142,992 A | 11/2000 | Cheng et al. | |
| 6,149,620 A | 11/2000 | Baker et al. | |
| 6,159,208 A | 12/2000 | Hovda et al. | |
| 6,225,883 B1 | 5/2001 | Wellner et al. | |
| 6,235,020 B1 | 5/2001 | Cheng et al. | |
| 6,238,391 B1 | 5/2001 | Olsen et al. | |
| 6,261,241 B1 | 7/2001 | Burbank et al. | |
| 6,296,636 B1 | 10/2001 | Cheng et al. | |
| 6,332,886 B1 | 12/2001 | Green et al. | |
| 6,348,051 B1 | 2/2002 | Farin et al. | |
| 6,394,956 B1 | 5/2002 | Chandrasekaran et al. | |
| 6,413,256 B1 | 7/2002 | Truckai et al. | |
| 6,419,674 B1 | 7/2002 | Bowser et al. | |
| 6,443,948 B1 | 9/2002 | Suslov | |
| 6,475,215 B1 | 11/2002 | Tanrisever | |
| 6,538,549 B1 | 3/2003 | Renne et al. | |
| 6,579,289 B2 | 6/2003 | Schnitzler | |
| 6,610,059 B1 | 8/2003 | West et al. | |
| 6,629,986 B1 | 10/2003 | Ross et al. | |
| 6,632,220 B1 | 10/2003 | Eggers et al. | |
| 6,656,195 B2 | 12/2003 | Peters et al. | |
| 6,669,694 B2 | 12/2003 | Shadduck | |
| 6,720,856 B1 | 4/2004 | Pellon et al. | |
| 6,780,178 B2 | 8/2004 | Palanker et al. | |
| 6,783,533 B2 | 8/2004 | Green et al. | |
| 6,821,275 B2 | 11/2004 | Truckai et al. | |
| 6,827,725 B2 | 12/2004 | Batchelor et al. | |
| 6,837,884 B2 | 1/2005 | Woloszko | |
| 6,837,888 B2 | 1/2005 | Ciarrocca et al. | |
| 6,890,332 B2 | 5/2005 | Truckai et al. | |
| 6,902,564 B2 | 6/2005 | Morgan et al. | |
| 6,979,332 B2 | 12/2005 | Adams | |
| 7,087,054 B2 | 8/2006 | Truckai et al. | |
| 7,112,200 B2 | 9/2006 | Cucin | |
| 7,150,747 B1 | 12/2006 | McDonald et al. | |
| 7,220,261 B2 | 5/2007 | Truckai et al. | |
| 7,309,849 B2 | 12/2007 | Truckai et al. | |
| 7,549,989 B2 | 6/2009 | Morgan et al. | |
| 7,674,263 B2 | 3/2010 | Ryan | |
| 7,678,069 B1 | 3/2010 | Baker et al. | |
| 7,713,269 B2 | 5/2010 | Auge, II et al. | |
| 7,717,710 B2 | 5/2010 | Danger et al. | |
| 7,744,595 B2 | 6/2010 | Truckai et al. | |
| 7,771,422 B2 | 8/2010 | Auge, II et al. | |
| 7,819,861 B2 | 10/2010 | Auge, II et al. | |
| 7,819,864 B2 | 10/2010 | Morgan et al. | |
| 7,955,331 B2 | 6/2011 | Truckai et al. | |
| 8,012,153 B2 | 9/2011 | Woloszko et al. | |
| 8,016,823 B2 | 9/2011 | Shadduck | |
| 8,062,319 B2 | 11/2011 | O'Quinn et al. | |
| 8,075,555 B2 | 12/2011 | Truckai et al. | |
| 8,192,424 B2 | 6/2012 | Woloszko | |
| 8,192,428 B2 | 6/2012 | Truckai et al. | |
| 8,221,404 B2 | 7/2012 | Truckai | |
| 8,323,280 B2 | 12/2012 | Germain et al. | |
| 8,333,763 B2 | 12/2012 | Truckai et al. | |
| 9,005,203 B2 * | 4/2015 | Nelson | A61B 17/1624 606/171 |
| 9,179,923 B2 | 11/2015 | Gubellini et al. | |
| 9,504,521 B2 | 11/2016 | Deutmeyer et al. | |
| 9,585,675 B1 | 3/2017 | Germain et al. | |
| 9,603,656 B1 | 3/2017 | Germain et al. | |
| 9,681,913 B2 | 6/2017 | Orczy-Timko et al. | |
| 2003/0014051 A1 | 1/2003 | Woloszko | |
| 2003/0083681 A1 | 5/2003 | Moutafis et al. | |
| 2003/0125727 A1 | 7/2003 | Truckai et al. | |
| 2003/0163135 A1 | 8/2003 | Hathaway | |
| 2004/0044341 A1 | 3/2004 | Truckai et al. | |
| 2004/0167427 A1 | 8/2004 | Quick et al. | |
| 2005/0015085 A1 | 1/2005 | McClurken et al. | |
| 2005/0075630 A1 | 4/2005 | Truckai et al. | |
| 2005/0228372 A1 | 10/2005 | Truckai et al. | |
| 2006/0058782 A1 | 3/2006 | Truckai et al. | |
| 2006/0074345 A1 | 4/2006 | Hibner | |

(56) References Cited

U.S. PATENT DOCUMENTS

| | | |
|---|---|---|
| 2006/0178670 A1 | 8/2006 | Woloszko et al. |
| 2006/0224154 A1 | 10/2006 | Shadduck et al. |
| 2007/0213704 A1 | 9/2007 | Truckai et al. |
| 2008/0003255 A1 | 1/2008 | Kerr et al. |
| 2008/0103494 A1 | 5/2008 | Rioux et al. |
| 2008/0188848 A1 | 8/2008 | Deutmeyer et al. |
| 2008/0208249 A1 | 8/2008 | Blain et al. |
| 2008/0249533 A1 | 10/2008 | Godin |
| 2009/0076498 A1 | 3/2009 | Saadat et al. |
| 2009/0209946 A1* | 8/2009 | Swayze ............ A61B 17/07207 606/1 |
| 2009/0270849 A1 | 10/2009 | Truckai et al. |
| 2010/0057078 A1* | 3/2010 | Arts ........................ A61B 10/06 606/41 |
| 2010/0087816 A1* | 4/2010 | Roy ................... A61B 18/1445 606/48 |
| 2010/0100091 A1 | 4/2010 | Truckai |
| 2010/0305565 A1 | 12/2010 | Truckai et al. |
| 2011/0160723 A1 | 6/2011 | Tullis et al. |
| 2011/0282373 A1 | 11/2011 | Chekan et al. |
| 2012/0209112 A2 | 8/2012 | Patel et al. |
| 2012/0245580 A1 | 9/2012 | Germain et al. |
| 2012/0310256 A1* | 12/2012 | Brisson .................. A61B 34/77 606/130 |
| 2012/0330292 A1 | 12/2012 | Shadduck et al. |
| 2013/0122461 A1 | 5/2013 | Shioiri |
| 2013/0172870 A1 | 7/2013 | Germain et al. |
| 2013/0253498 A1 | 9/2013 | Germain et al. |
| 2013/0267937 A1 | 10/2013 | Shadduck et al. |
| 2013/0296847 A1 | 11/2013 | Germain et al. |
| 2013/0296849 A1 | 11/2013 | Germain et al. |
| 2013/0317492 A1* | 11/2013 | Truckai .................. A61B 18/08 606/29 |
| 2013/0317493 A1 | 11/2013 | Truckai et al. |
| 2013/0331833 A1 | 12/2013 | Bloom |
| 2014/0012238 A1 | 1/2014 | Chen et al. |
| 2014/0025046 A1* | 1/2014 | Williams ......... A61B 17/07207 606/1 |
| 2014/0100567 A1 | 4/2014 | Edwards et al. |
| 2014/0114300 A1 | 4/2014 | Orczy-Timko et al. |
| 2014/0336643 A1 | 11/2014 | Orczy-Timko et al. |
| 2015/0209061 A1* | 7/2015 | Johnson ............ A61B 17/32002 606/171 |
| 2015/0272569 A1* | 10/2015 | Leimbach ...... A61B 17/320016 227/175.1 |
| 2016/0081737 A1 | 3/2016 | Germain et al. |
| 2016/0113706 A1 | 4/2016 | Truckai et al. |
| 2016/0157916 A1 | 6/2016 | Germain et al. |
| 2017/0027599 A1 | 2/2017 | Bek et al. |
| 2017/0128083 A1 | 5/2017 | Germain et al. |
| 2017/0172648 A1 | 6/2017 | Germain et al. |
| 2017/0224368 A1 | 8/2017 | Germain et al. |
| 2017/0252099 A1 | 9/2017 | Orczy-Timko et al. |
| 2017/0258512 A1 | 9/2017 | Germain et al. |
| 2017/0258519 A1 | 9/2017 | Germain et al. |
| 2019/0008537 A1* | 1/2019 | Kirstgen ............ A61B 17/2909 |
| 2019/0008541 A1* | 1/2019 | Norton ............... A61B 18/1445 |

FOREIGN PATENT DOCUMENTS

| | | |
|---|---|---|
| WO | WO-0053112 A2 | 9/2000 |
| WO | WO-0062685 A1 | 10/2000 |
| WO | WO-0053112 A3 | 12/2000 |
| WO | WO-2007073867 A1 | 7/2007 |
| WO | WO-2014165715 A1 | 10/2014 |
| WO | WO-2017156335 A1 | 9/2017 |
| WO | WO-2017156343 A1 | 9/2017 |
| WO | WO-2017180654 A1 | 10/2017 |

OTHER PUBLICATIONS

International Search Report and Written Opinion dated Jul. 15, 2016 for International PCT Patent Application No. PCT/US2016/027157.

International Search Report and Written Opinion dated Mar. 8, 2017 for International PCT Patent Application No. PCT/US2016/058179.

International Search Report and Written Opinion dated May 16, 2017 for International PCT Patent Application No. PCT/US2017/016002.

International Search Report and Written Opinion dated May 22, 2017 for International PCT Patent Application No. PCT/US2017/021675.

International Search Report and Written Opinion dated May 23, 2012 for International PCT Patent Application No. PCT/US2012/023390.

International Search Report and Written Opinion dated Aug. 1, 2017 for International PCT Patent Application PCT/US2017/021687.

International Search Report and Written Opinion dated Aug. 22, 2017 for International PCT Patent Application No. PCT/US2017/027053.

International Search Report and Written Opinion dated Nov. 29, 2016 for International Application No. PCT/US2016/058145.

International search report dated Jan. 14, 2002 for PCT/US2001/025409.

Kim, et al. Optical feedback signal for ultra short pulse ablation of tissue. Appl. Surface Sci. 1998; 127-129:857-862.

Notice of Allowance dated Jan. 6, 2017 for U.S. Appl. No. 14/960,084.

Notice of Allowance dated Feb. 8, 2017 for U.S. Appl. No. 14/977,256.

Notice of Allowance dated Feb. 16, 2017 for U.S. Appl. No. 15/096,546.

Notice of Allowance dated Dec. 2, 2016 for U.S. Appl. No. 14/977,256.

Notice of Allowance dated Dec. 30, 2016 for U.S. Appl. No. 14/977,256.

Office Action dated May 3, 2016 for U.S. Appl. No. 14/960,084.

Office Action dated Jul. 28, 2016 for U.S. Appl. No. 14/977,256.

Office Action dated Aug. 18, 2016 for U.S. Appl. No. 14/960,084.

Office Action dated Sep. 26, 2016 for U.S. Appl. No. 15/096,546.

Pedowitz, et al. Arthroscopic surgical tools: a source of metal particles and possible joint damage. Arthroscopy. Sep. 2013;29(9):1559-65. doi: 10.1016/j.arthro.2013.05.030. Epub Jul. 30, 2013.

Smith & Nephew. Dyonics Bonecutter Electroblade. Webpage. Accessed Feb. 28, 2017. 2 pages. URL:< http://smith-nephew.com/professional/products/all-products/dyonics-bonecutter-electroblade>.

Tucker et al. Histologic characteristics of electrosurgical injuries. J. Am. Assoc. Gyneco. Laproscopy. 1997; 4(2):857-862.

Volpato, et al., Application of Zirconia in Dentistry: Biological, Mechanical and Optical Considerations. Advances in ceramics—electric and magnetic ceramics, bioceramics, ceramics and environment. Sep. 2011.

* cited by examiner

ARTHROSCOPIC DEVICES AND METHODS

CROSS-REFERENCE TO RELATED APPLICATIONS

This application claims the benefit of provisional application No. 62/321,114, filed on Apr. 11, 2016, provisional application No. 62/325,224, filed on Apr. 20, 2016, and provisional application No. 62/325,326, filed on Apr. 22, 2016, the full disclosures of which are incorporated herein by reference.

BACKGROUND OF THE INVENION

1. Field of the Invention

This invention relates to arthroscopic tissue cutting and removal devices by which anatomical tissues may be cut and removed from a joint or other site. More specifically, this invention relates to instruments with a motor driven openable-closeable jaw that cuts tissue.

2. Description of the Background Art

In several surgical procedures including a meniscectomy, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

The need exists for arthroscopic cutters that remove soft tissue rapidly.

SUMMARY OF THE INVENTION

In a first aspect, the present invention provides an arthroscopic cutter comprising a handpiece having a motor drive. A shaft assembly includes an openable-closable jaw structure at a working end of the shaft and a hub at a hub end of the shaft. The hub is configured for detachable coupling to the handpiece, and the motor drive is configured to couple to the jaw structure when the hub is coupled to the handpiece. In particular, when coupled to the jaw structure, the motor drive can continuously, intermittently, or otherwise selectively open and close individual jaws of the jaw structure to cut tissue, typically in a series of sequential resections or "bites" as the shaft assembly is advanced to engage the jaw structure against target tissue.

In a specific aspect of the arthroscopic cutter, the jaw structure may include sharp edge portions configured for cutting tissue, typically formed on at least one jaw of the jaw structure. The hub structure may also include a gear mechanism configured to amplify an output torque of the motor drive to increase a closing force of the jaw structure to enhance its ability to resect, cut, or otherwise remove tissue. Typically, the gear mechanism will increase an "effective" torque delivered by the jaw structure to the tissue by a factor of at least 10 when compared to the torque delivered by a spindle or other rotational drive element of the motor drive, often by a factor of at least 20, frequently by a factor of at least 40, and in some instances by a factor of at least 60, or more. That is, the torque applied by the jaws of the jaw structure as they pivot about a pivot point will have a torque which is greater than the torque provided by the motor drive by the factors recited above. In this way, the gear mechanism can increase the motor output torque to apply a jaw structure torque of at least 10 in-lbs, often at least 40 in-lbs, frequently at least 60 in-lbs, and sometimes at least 80 in-lbs, or greater. Exemplary gear mechanisms will include a planetary gear set.

The arthroscopic cutters of the present invention will usually include a mechanism for converting a rotational motion of the motor drive to a linear motion to reciprocate an actuator member for opening and closing the jaws of the jaw structure. In such cases, the gear mechanism is typically operatively coupled to the mechanism for converting the rotational motion into linear motion.

In still further exemplary embodiments, the motor drive is configured to open and close the jaw structure at a rate of at least 1 CPS (cycle(s) per second), often at a rate in the range of between 1 CPS and 100 CPS, frequently at a rate in the range between 1 CPS and 10 CPS, and the like.

Other exemplary arthroscopic cutters of the present invention may include a passageway extending through the shaft assembly to the working end of the shaft. The passageway is typically configured for connection to a negative pressure source which can provide for continuous or periodic aspiration or suction of resected tissue from the operative site.

In additional exemplary embodiments, the arthroscopic cutters of the present invention may further comprise a processor configured to control the motor drive, e.g., to stop and/or start movement of a first jaw in the jaw structure relative to a second jaw of the jaw structure. Typically, the movement may be stopped in a variety of positions, such as one or more default positions. For example, a default position may be with the jaws open. In other cases, a default position may be with the jaws closed or in any other relative position between open and closed. Typically, a sensor in the handpiece will be connected to the controller and configured to sense jaw position, e.g., using a magnet coupled to the jaw structure (in one instance carried by a separate moving member coupled to the jaw structure) to indicate default and non-default positions, thus allowing motion to be stopped at a desired position.

In still further exemplary embodiments, the arthroscopic cutters of the present invention may include an actuator for actuating the motor drive to open and close the jaw structure, for example at a rate of at least 1 CPS. Such actuators may also be configured to move the jaw structure to a jaw-open position, to a jaw-closed position as well as for other purposes, such as for actuating a negative pressure source, for actuating both the motor drive and a negative pressure source, for modulating the negative pressure source in response to actuation in the motor drive, and the like. In other instances, the processor may be configured to modulate the negative pressure source relative to a fully open position, a partially open position, or a closed position of the jaw structure.

The arthroscopic cutters of the present invention, in still other embodiments, may include radio frequency (RF) electrode edge portions configured for cutting or otherwise resecting tissue. Alternative, the jaw structures may have first and second jaws including honed, or other scissor-like edge portions for shearing tissue. In still other embodiments, the jaw structure may have at least one cup-shaped jaw adapted for cutting and capturing tissue. In yet other embodiments, the jaw of the jaw structure may have a metal cutting edge, a ceramic cutting edge, or may simply comprise a ceramic material.

In a second aspect, the present invention provides methods for performing a meniscectomy. Such methods comprise providing a handpiece with a motor drive. The probe is coupled to the handpiece, where the probe has a working end with openable-closeable jaws configured to resect tissue. The motor drive is configured to open and close the jaws when the handpiece is coupled to the probe. The working end may then be advanced into a patient's joint to engage the jaws against meniscal tissue. The meniscal tissue may then be resected by actuating the motor drive to open and close the jaws.

In specific embodiments, the methods for performing meniscectomy may further comprise controlling the motor drive with a controller to actuate the jaws to resect the meniscal tissue in a single bite, or in multiple bites. For example, the motor drive may be controlled to open and close the jaws at a rate of at least 1 CPS, often at a rate of between 1 CPS and 100 CPS. At the actuating step may further comprise activating a negative pressure source in communication with an interior passageway of the probe to suction resected meniscal tissue from the working end.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to tissue cutting and removal devices and related methods of use. Variations of the invention will now be described to provide an overall understanding of the principles of the form, function and methods of use of the devices disclosed herein. In general, the present invention provides an arthroscopic cutter or punch for cutting tissue that is disposable and is configured for detachable coupling to a non-disposable handle and motor drive component. This description of the general principles of this invention is not meant to limit the inventive concepts in the appended claims.

FIGS. 1-5B illustrates a tissue cutting probe 100 with a jaw structure 108 that is motor driven to close and open the jaws in a single actuation that applies high cutting forces, or alternatively, the motor drive can be actuated to close and open the jaws sequentially at 1 CPS to 100 CPS (cycle per second) to progressively nibble or cut tissue. The probe can be used in arthroscopy and other fields, for example, ENT, gynecology and urology.

Figure 1:
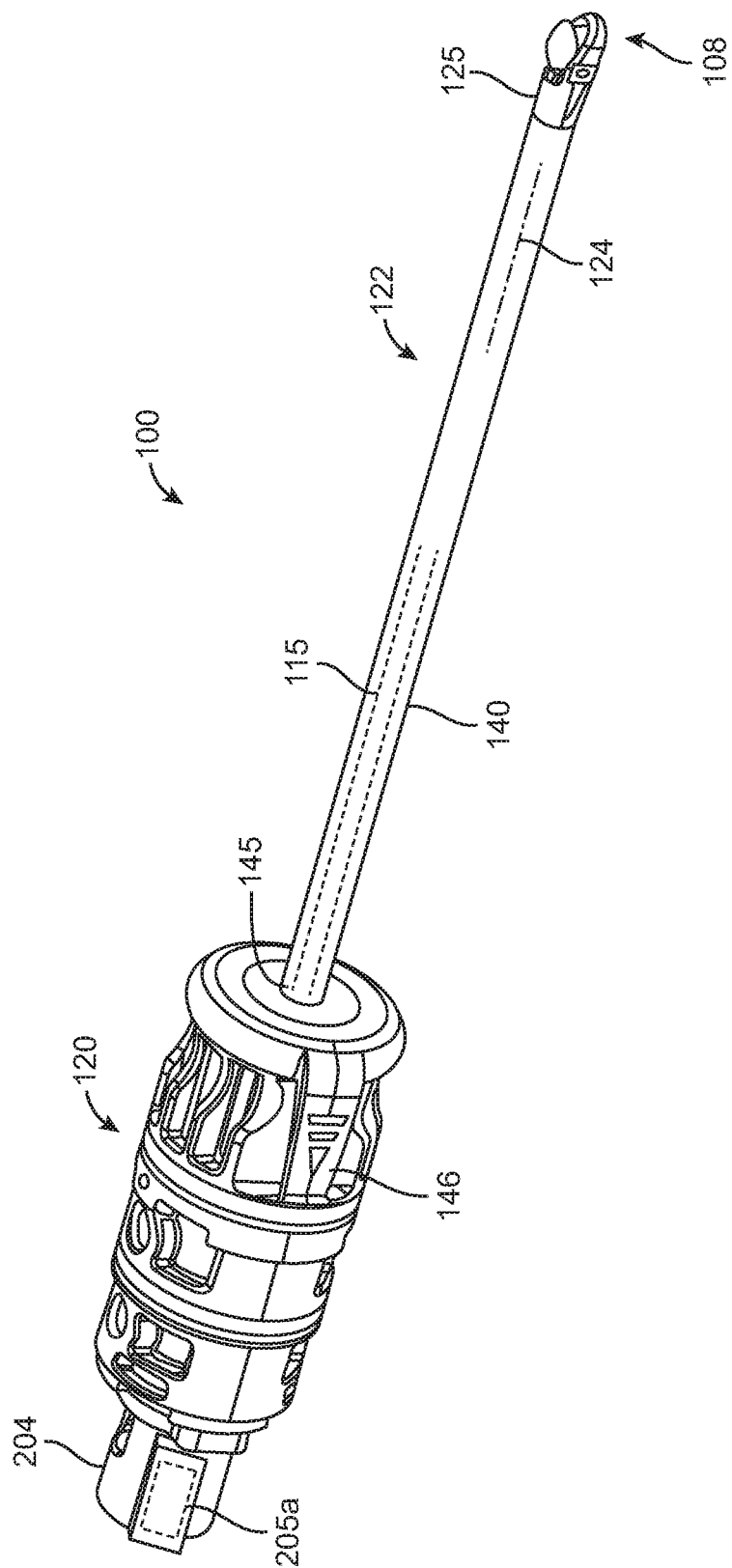
FIG. 1 is a perspective view of a disposable arthroscopic cutter or probe with a working end comprising a jaw structure having cutting edges.
Figure 2:
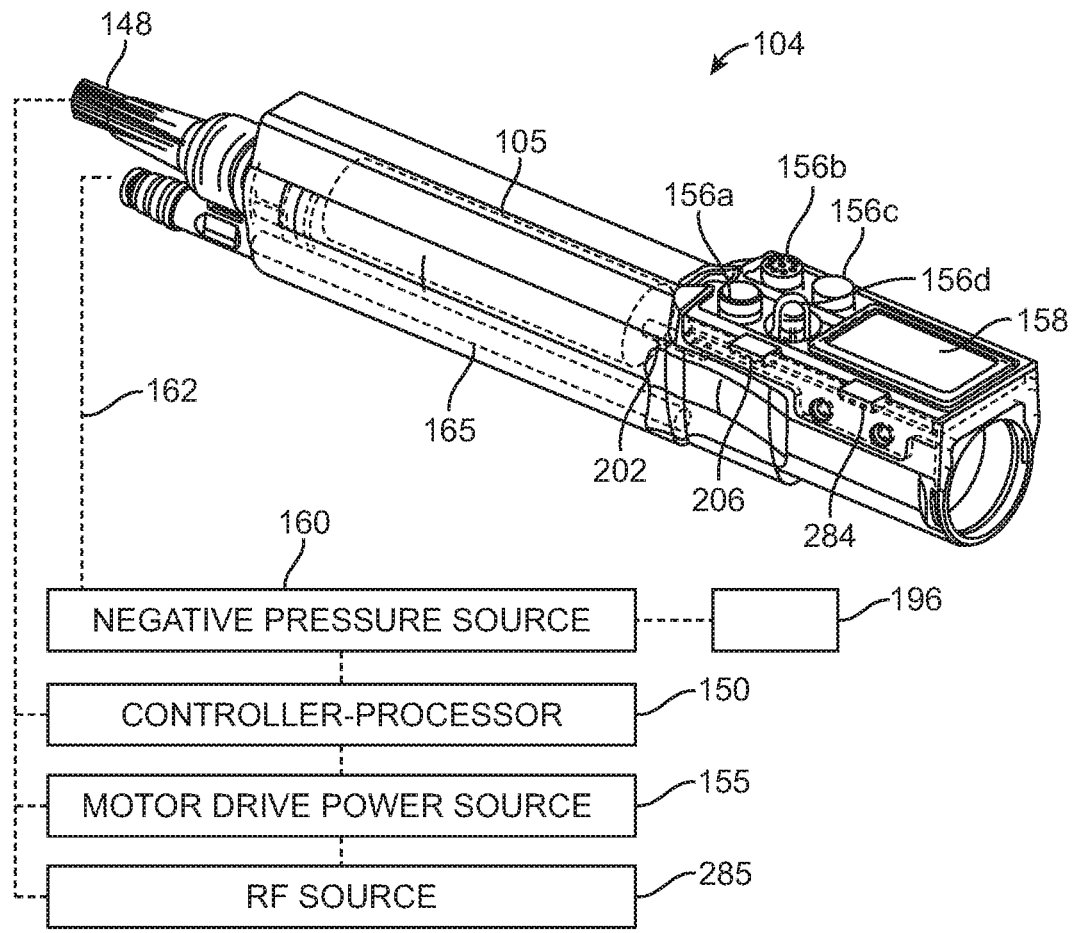
FIG. 2 is a perspective view of a handpiece with a motor drive to which the cutter of FIG. 1 can be coupled, with the handle body including an LCD screen for displaying operating parameters of device during use together with a joystick and mode control actuators on the handle.

FIG. 1 shows the disposable cutting probe 100 that is adapted for detachable coupling to a handpiece 104 and motor drive unit 105 therein as shown in FIG. 2. In the variation shown in FIGS. 1 and 3, the upper jaw 110 and lower jaw 112 are configured as cup-shaped jaws to assist in capturing and extracting tissue chips through an interior passageway 115 as will be described below (see FIGS. 5A-5B).

Referring to FIG. 1, it can be seen that cutting probe 100 has a proximal hub 120 that can be detachably coupled to the handle or handpiece 104 of FIG. 2. In the variation of FIG. 1, the probe 100 has a shaft 122 that extends about longitudinal axis 124 to a working end 125 that comprises the openable-closeable jaw structure 108 that is coupled to the motor drive 105. The shaft 122 comprises an outer sleeve 140 and an inner actuation member 142 that is adapted to reciprocate in bore 144 of the outer sleeve 140. The proximal end 145 of outer sleeve 140 is coupled in a fixed manner to the hub 120 which can be an injection molded plastic, for example, with the outer sleeve 140 insert molded therein. The outer sleeve 140 typically can be a thin wall stainless steel tube, but other materials can be used such as ceramics, metals, plastics or combinations thereof. In this variation, the reciprocation of actuation member 142 is adapted to close and open to jaw structure 108 as can be understood from FIGS. 5A-5B. Referring to FIGS. 1 and 2, the hub 120 is configured with snap-fit features 146, or other suitable features, for detachably locking the hub 120 into the handpiece 104.

In FIG. 2, it can be seen that the handpiece 104 is operatively coupled by electrical cable 148 to a controller-processor 150 which controls the motor drive unit 105. The cable 148 also couples power from electrical power source 155 to the motor drive 105. Any of the actuator buttons 156a-156d on the handpiece 104 can be used to select operating modes, such as a single open-close actuation of the jaws, or a continuous sequence of opening and closing the jaws. Further, an actuator button can be used to modulate the CPS of opening and closing the jaws. The various modes can be displayed on the LCD 158. FIG. 2 further shows that negative pressure source 160 is coupled to aspiration tubing 162 which communicates with a flow channel 165 in the handpiece 104 and passageway 115 in actuating member 142 which extends to the working end 125.

Figure 3:
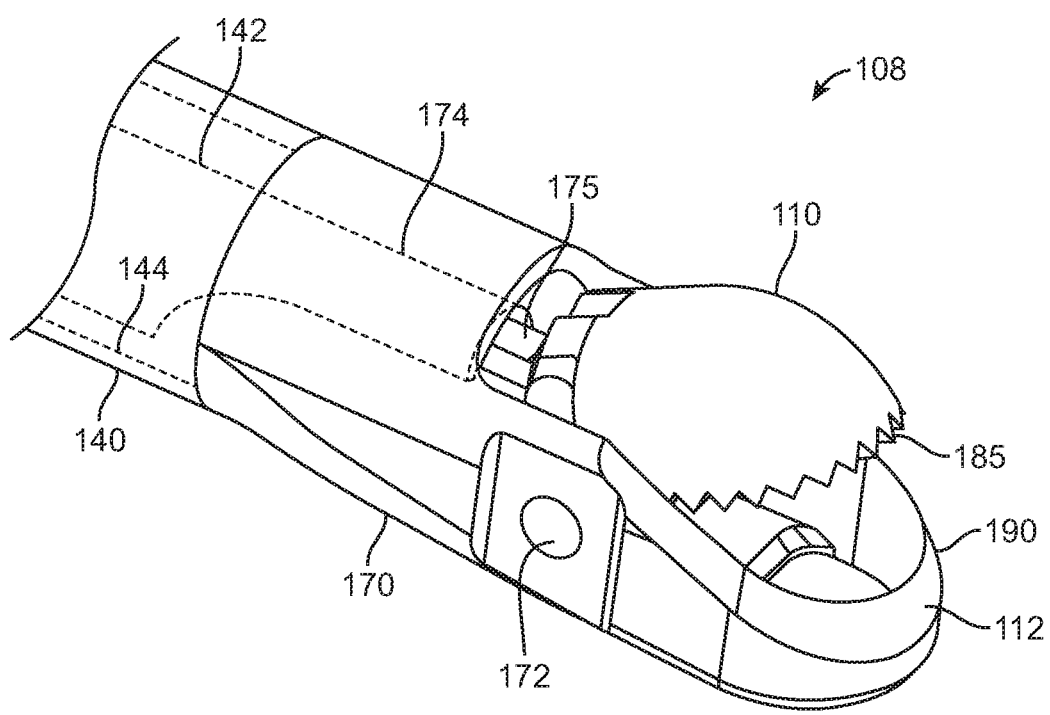
FIG. 3 is a detailed view of a working end of a probe constructed in accordance with the principles of the present invention.
Figure 4A:
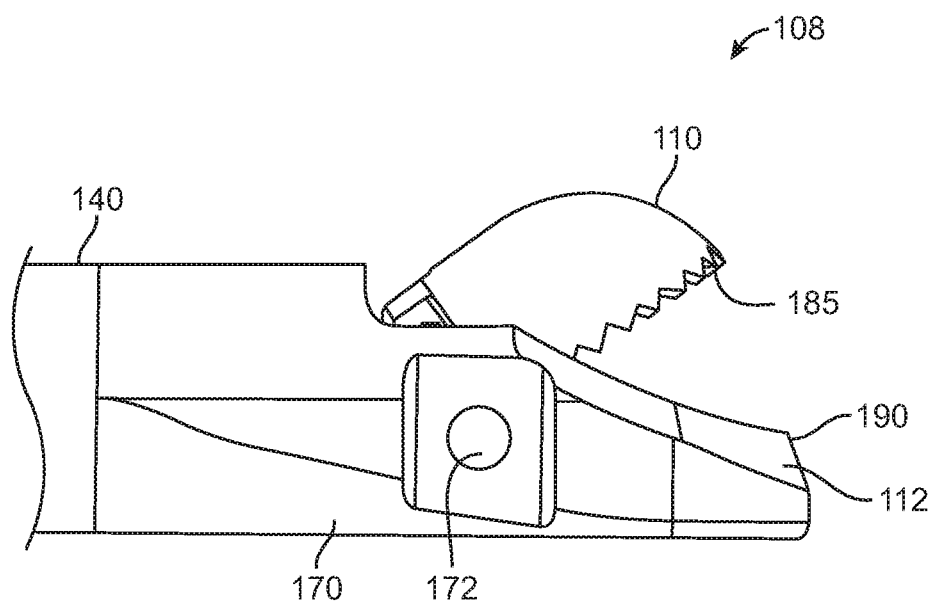
FIG. 4A is an enlarged side view of the working end of the probe of FIG. 1 in a jaw-open position.
Figure 4B:
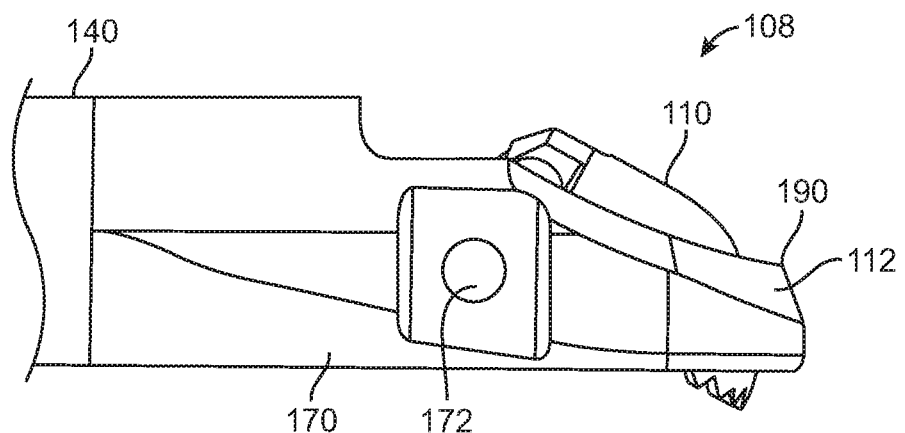
FIG. 4B is a side view of the working end of FIG. 4A in a jaw-closed position.
Figure 5A:
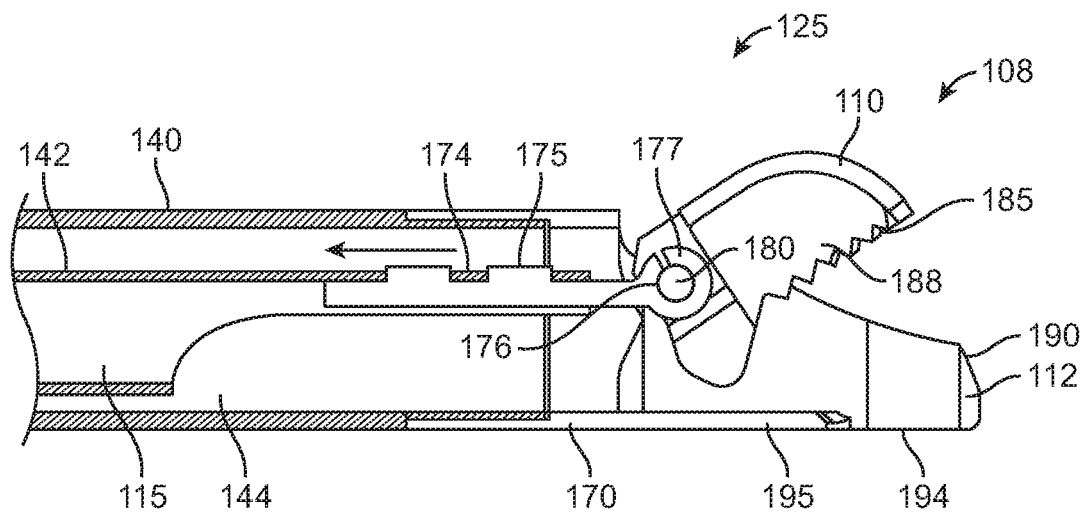
FIG. 5A is a longitudinal sectional view of the working end of FIG. 4A in the jaw-open position showing a portion of the jaw actuation mechanism.
Figure 5B:
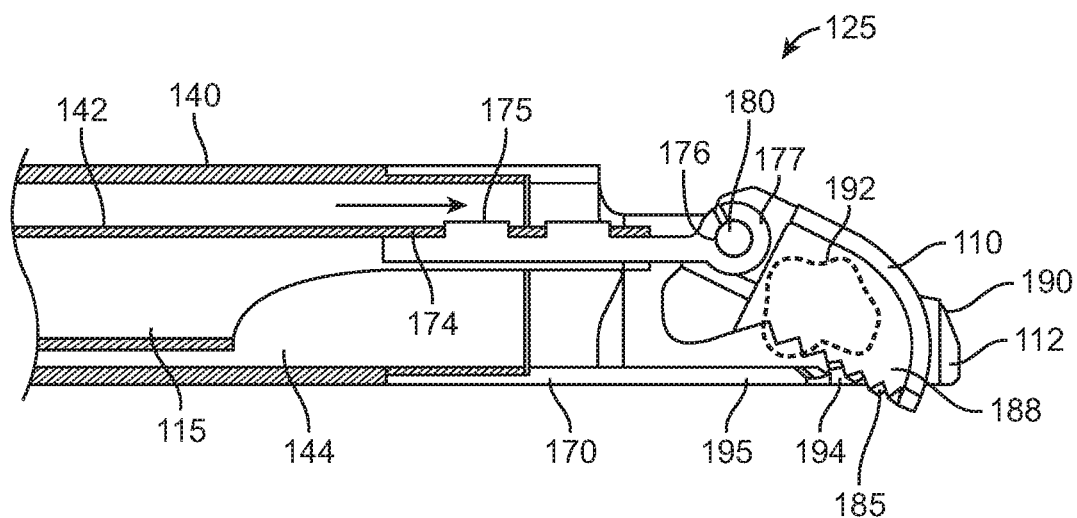
FIG. 5B is a sectional view of the working end of FIG. 4B in the jaw-closed position.

As can be seen in FIGS. 1, 3 and 4A-5B, the second or lower jaw 112 and lower jaw housing 170 is immobile and fixed to outer sleeve 140. The upper jaw 110 pivots around pivot point 172 in the lower jaw housing 170. The actuation member 142 can comprise a sleeve with passageway 115 therein and a distal end 174 coupled to an actuation rod 175 with a transverse bore 176 in a collar portion 177 that surrounds a transverse shaft 180 in the upper jaw 110. Thus, it can be seen how reciprocation of the actuating member 142 can move the first or upper jaw 110 relative to the second or fixed lower jaw 112. It should be appreciated that both the upper and lower jaw members of the jaw structure can be moveable as is known in biopsy punches and similar end effectors on medical cutting probes. In FIG. 3, the upper jaw 110 is fabricated of a high-strength metal, but it should be appreciated that such a jaw also can be fabricated out of a ceramic, such as the ceramics with a high fracture toughness as described in co-authored U.S. Pat. Nos. 9,585,675 and 9,603,656, which are incorporated herein by this reference. The lower jaw 112 likewise can be fabricated from a metal or a suitable ceramic with a sharp cutting edge.

Referring to FIGS. 3, 4A-4B and 5A-5B, it can be seen that upper jaw 110 is cup-shaped as is known in biopsy punches or meniscal punches for resecting tissue. The upper jaw 110 has a gripping and/or cutting edge 185 that extends in a U-shape around interior cavity 188 of the jaw. The lower jaw 112 has a cooperating U-shaped sharp cutting edge 190. It can be understood from FIGS. 4A-5B, the closing of jaw structure 108 shears tissue between cutting edges 185 and 190 to thus capture a tissue chip 192 (FIG. 5B) in the jaw's interior cavity 188. In the closed position of FIGS. 4B and 5B, it can be seen that the U-shaped edge 185 of the upper jaw 110 passes into U-shaped slot 194 in baseplate portion 195 of the lower jaw housing 170. Thereafter, the tissue chip 192 can be aspirated through interior passageway 115 by the negative pressure source 160 and be collected in a collection reservoir 196 (see FIG. 8).

Figure 6:
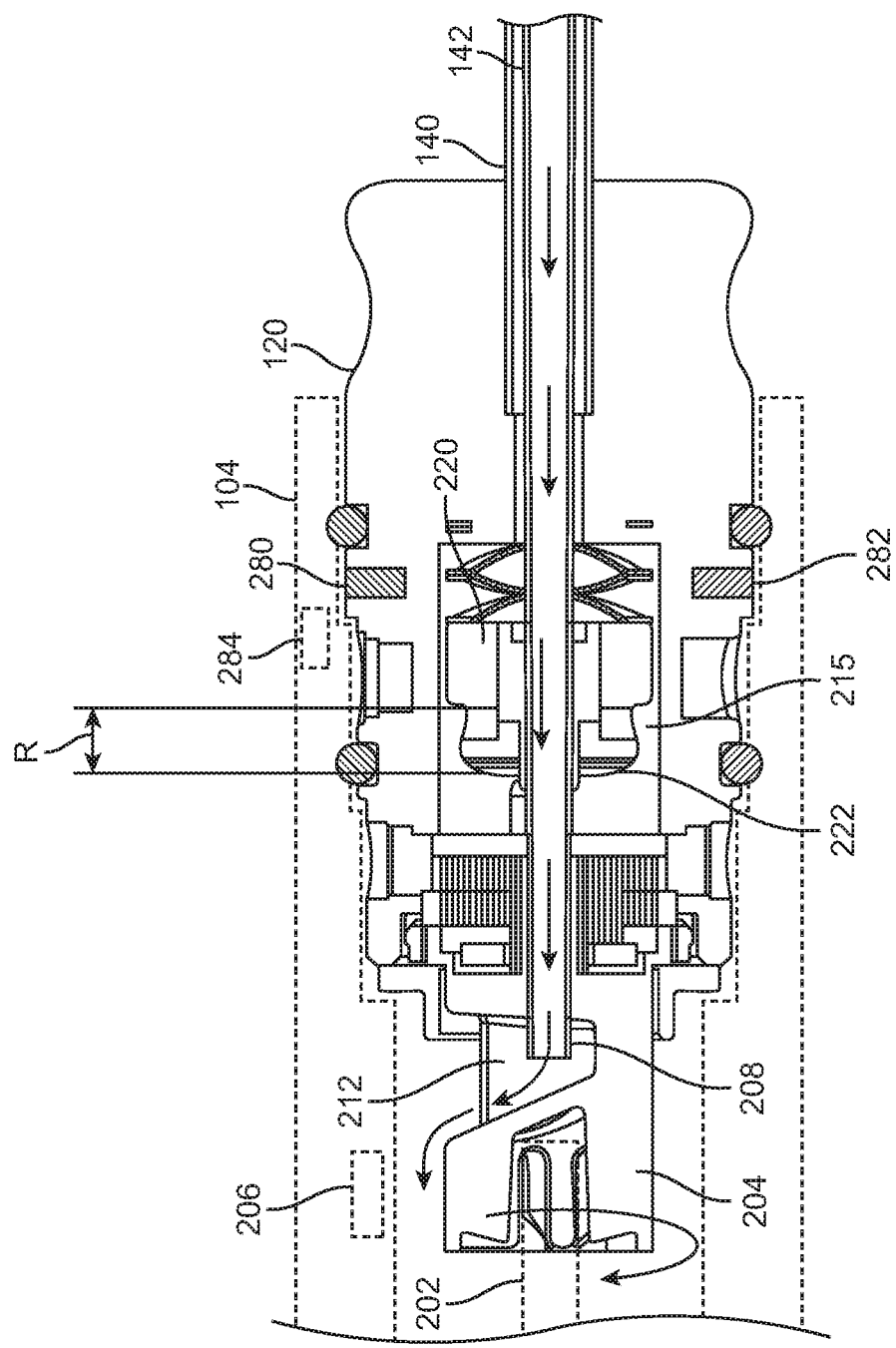
FIG. 6 is a longitudinal sectional view of the hub of the probe of FIG. 1 taken along line 6-6 of FIG. 1 showing a gear mechanism and a mechanism for converting rotational motion to linear motion to actuate the jaw structure at a selected CPS rate (cycles per second).
Figure 7A:
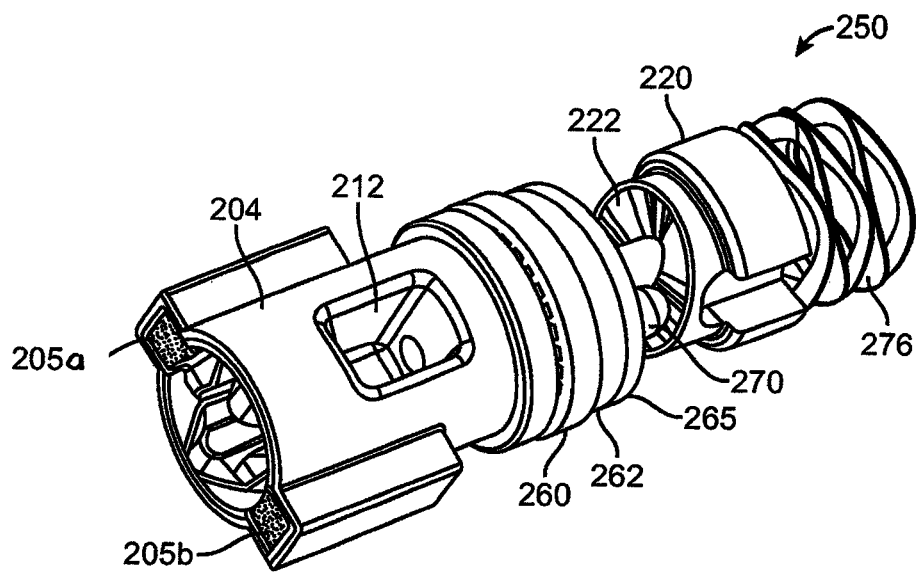
FIG. 7A is a perspective view of the planetary or epicyclic gear mechanism of the probe hub of FIG. 6 and the rotation-to-linear motion mechanism.
Figure 7B:
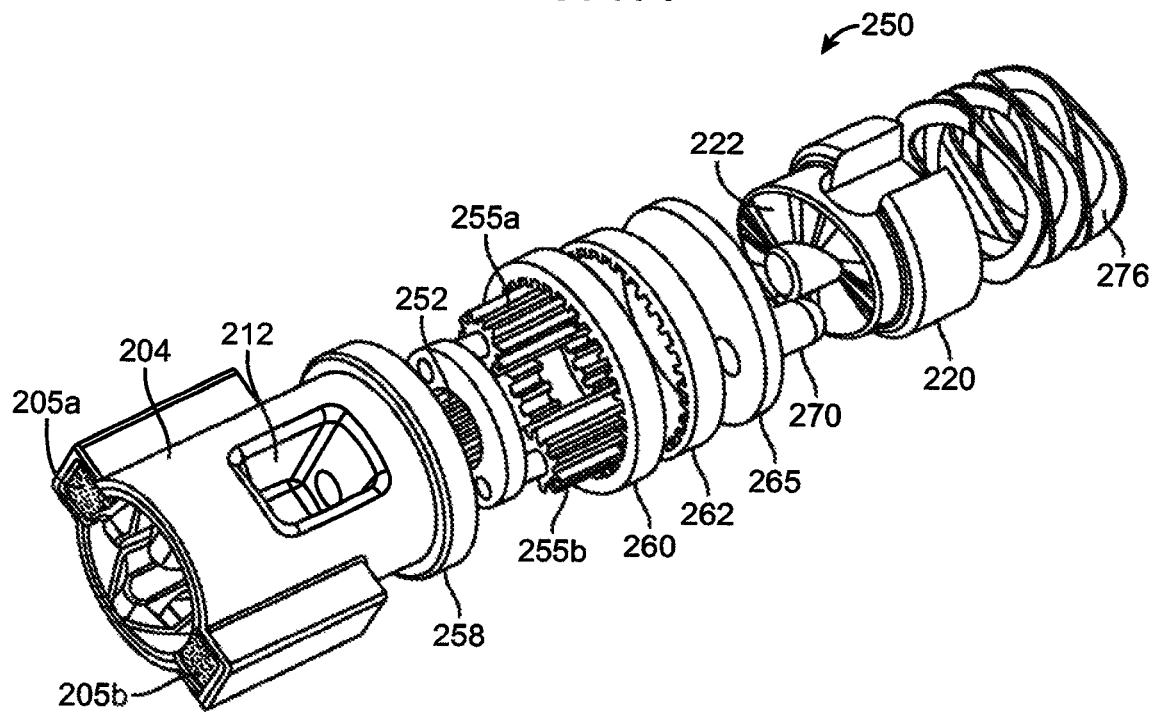
FIG. 7B is an exploded view of the components of the epicyclic gear mechanism of FIG. 7A.

Now turning to FIGS. 6 and 7A-7B, the mechanism that converts the rotation of the rotating shaft 202 of motor drive 105 to linear motion of actuation member 142 can be described. In one aspect of the invention, when cutting somewhat hard tissue such as meniscus, what is needed is an amplification of force that can be applied by the cutting edges of the jaw structure 108 against the targeted tissue. In FIGS. 6 and 7A, it can be seen rotatable drive coupling 204 is adapted for engaging the motor shaft 202 as is known in the art. The drive coupling 204 carries magnets 205a in 205b that cooperate with a Hall sensor 206 in the handpiece (FIGS. 2 and 6) to the acquire signals relating to the rotational orientation of drive coupling 204. The controller and processor 150 then can determine the open and closed positions of the jaw structure 108 depending on the rotational orientation of the coupling 204. It can be seen that the proximal end 208 of the actuator member 142 extends through the drive coupling 204 to the opening 212 in the side of drive coupling 204 to allow tissue chips (e.g., tissue chip 192 in FIG. 5B) to be extracted through the hub 120. The actuation member 142 is fixed in a collar 220 having a cam surface 222 that rotates in interior chamber 215 of the hub 120 (FIG. 6).

In one aspect of the invention, the drive coupling 204 engages the gear reduction mechanism comprising an epicyclic gear train assembly 250 which also may be called a planetary gear mechanism. FIG. 7A shows the epicyclic gear train assembly 250 removed from the hub 120 of FIG. 6. FIG. 7B depicts the gear train 250 of FIG. 7A in an exploded view showing the sun gear 252, the planet gears 295a and 295b, carrier ring 258, stationary output ring gear 260, output ring gear 262 and output ring gear transfer plate 265 as is known in the art. FIGS. 7A-7B also show a projecting element or stud 270 that interfaces with the angled cam surface 222 on rotating collar 220 that is adapted to convert rotational motion to linear motion. Thus, rotation of rotating motor shaft 202 rotates the sun gear 252 and planet gears 295a and 295b, to provide gear reduction and ultimately rotate the output ring gear transfer plate 265 and rounded-end stud 270 to actuate the non-rotatable cam surface 222, which in turn reciprocates the actuator member 142. A spring 276 is provided to urge the rotating collar 220 carrying the cam surface 222 toward a proximal or retracted position in the interior chamber 215 of the hub 120. The stroke of reciprocation R is shown in FIG. 6 which is required to open and close the jaw structure 108.

In one aspect of the invention, the epicyclic gear mechanism of FIGS. 6-7B is configured for amplifying the output torque of the motor drive to increase closing forces of the jaw structure. In one variation, the gear mechanism increases the motor output torque by a factor of at least 10 or by a factor of at least 20. In some variations, the gear mechanism increases the motor output torque by at a factor of at least 40, and often by a factor of at least 60. In another aspect, the gear mechanism increases the motor output torque to at least 10 in-lbs, at least 40 in-lbs, at least 60 in-lbs, or at least 80 in-lbs.

In another aspect of the invention, the processor 150 is adapted to operate the motor drive 105 to move the jaw structure between open and closed positions at a rate of at least 1 CPS (cycles per second). Typically, the motor drive is configured to move the jaw structure between open and closed positions at a rate between 1 CPS and 100 CPS, and often at a rate between 1 CPS and 10 CPS. The processor also can be configured to control the motor drive 105 to stop movement of a first jaw relative to a second jaw in a selected default position, which typically is a closed position but also can be an open position. It can be understood that the jaw must be in a closed position for introduction into a patient's body, therefore a closed position is the typical default position. However, when the physician has positioned the working end 125 in a treatment site, the jaw structure 108 preferably would be in an open position. Therefore, a button (156a-156d) on the handpiece 104 can be adapted to move the jaws from the default closed position to the open position.

In use, an actuator button (156a-156d) can be used to close and open to jaw structure 108 in a single bite, or the actuator button can sequentially close and open the jaws at a selected rate. In one variation, an actuator button such as a joystick can increase the closing opening rate from a lower rate to a higher rate. Typically, an actuator button on the handpiece 104 actuates the motor drive 105 to move the jaw structure 108 between the jaw-open and jaw-closed positions at a rate of at least 1 CPS (cycles per second). More often, the rate of actuation is between 2 CPS and 10 CPS, although the rate could be higher, for example up to 100 CPS.

In another aspect of the invention, the processor 150 can be configured to modulate the negative pressure source 160 in response to actuation of the motor drive 105, so the negative pressure is actuated contemporaneously with closing and opening jaws. In another variation, the processor 150 can be configured to modulate the negative pressure source relative to a fully open jaw position, a partially open jaw position or a closed jaw position.

Figure 8:
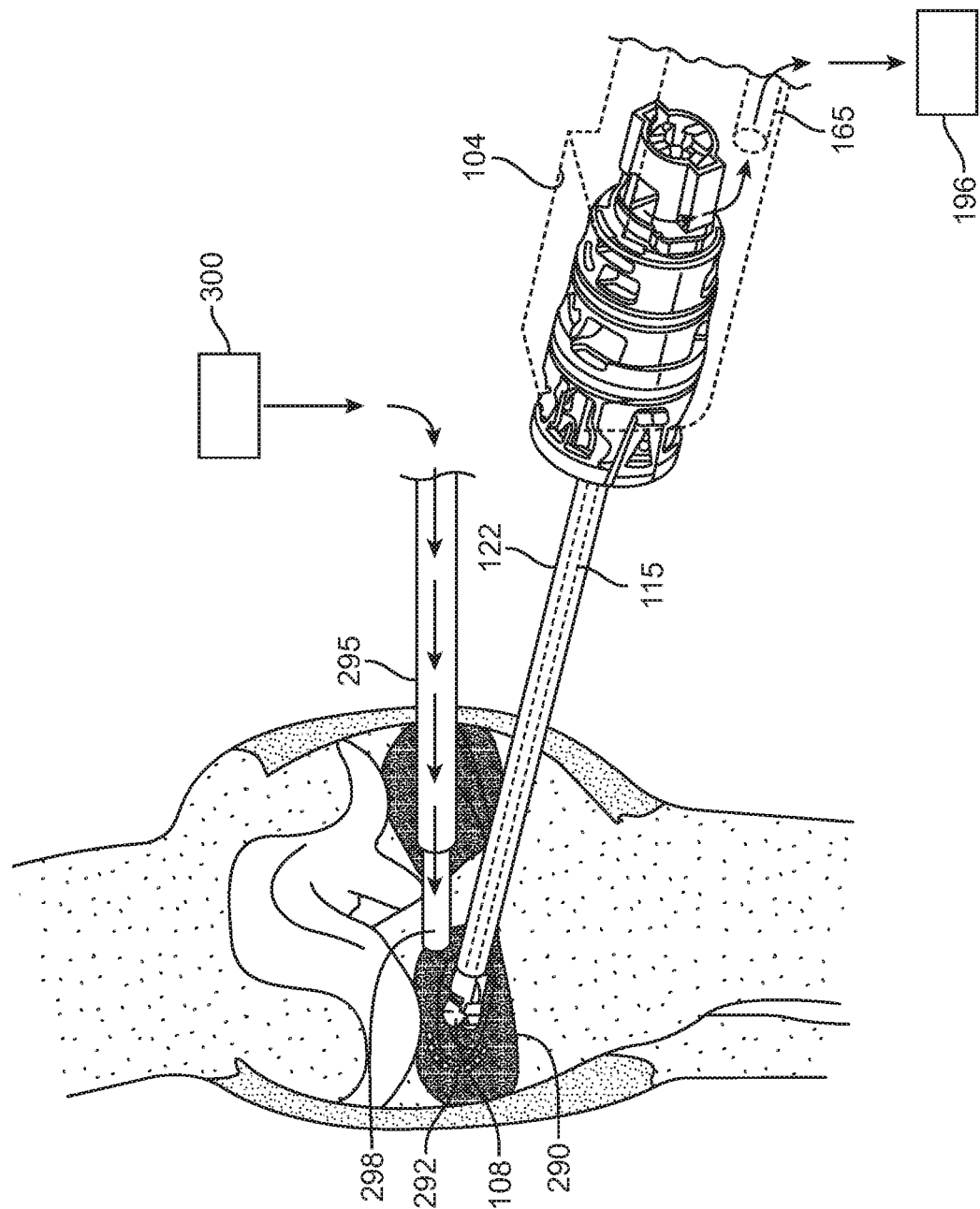
FIG. 8 is a schematic view of a method of using the probe of FIGS. 1-6 in a meniscectomy procedure.

Now referring to FIGS. 1, 2 and 8, a method of using probe 100 of FIG. 1 is shown schematically in a meniscectomy procedure. First, the physician inserts the probe 100 of FIG. 1 into the handpiece 104 of FIG. 2. Magnets 280 and 282 in the probe hub 120 (FIG. 6) are oriented relative to relative to a Hall sensor 284 in the handpiece (FIG. 2) such that the controller-processor 150 identifies the type of probe coupled to the handpiece 104 and the up or down orientation of the probe. The use of a Hall sensors and magnets in a probe hub for (i) device identification and (ii) positioning of working end components of arthroscopic tools is further described in co-pending U.S. patent application Ser. No. 15/454,432 filed Mar. 9, 2017 (Atty. Docket No. 41879-715.201) which is incorporated herein by this reference. Based on such a device identification, the controller then selects the appropriate processor algorithms for operating the probe 100. The handpiece 104 is adapted to receive and operate multiple different tools including rotating mechanical shavers, reciprocating electrosurgical shavers, hook shaped electrosurgical devices and articulating radiofrequency devices. Therefore, device identification is necessary because each different type of probe requires different processor algorithms to control the motor drive 105, the negative pressure source 160 and potentially the RF source 285, as will be described below.

Returning to FIG. 8, the cut-away view of the patient's knee shows the meniscus 290 with a "bucket handle" tear indicated at 292. The physician introduces a cannula 295 into the joint space and then advances an endoscope 298 through the cannula to view the treatment site. A fluid source 300 is coupled to the cannula 295 to introduce a distention fluid, such as saline, into the treatment site. Thereafter, the physician introduces the shaft 122 and working end of the probe 100 into the treatment site with the jaw structure 108 in the default closed position. Thereafter as shown in FIG. 8, the physician uses an actuator button (156*a*-156*d*) on the handpiece 104 (FIG. 2) to move the jaw structure 108 to the jaw-open position. Next, the physician manipulates working end to position the open jaw structure 108 over the meniscus tissue of the tear 292 targeted for resection. Thereafter, the physician uses an actuator button (156a-156d) to close the jaw structure with high closing forces in a single bite, or sequentially in repeated bites. The physician can then move the jaw structure 108 about the treatment site to remove targeted tissue. The resected tissue chips are then aspirated through the interior channel 115 of the probe 100 and flow channel 165 of handpiece 104 to be collected in collection reservoir 196.

Figure 9A:
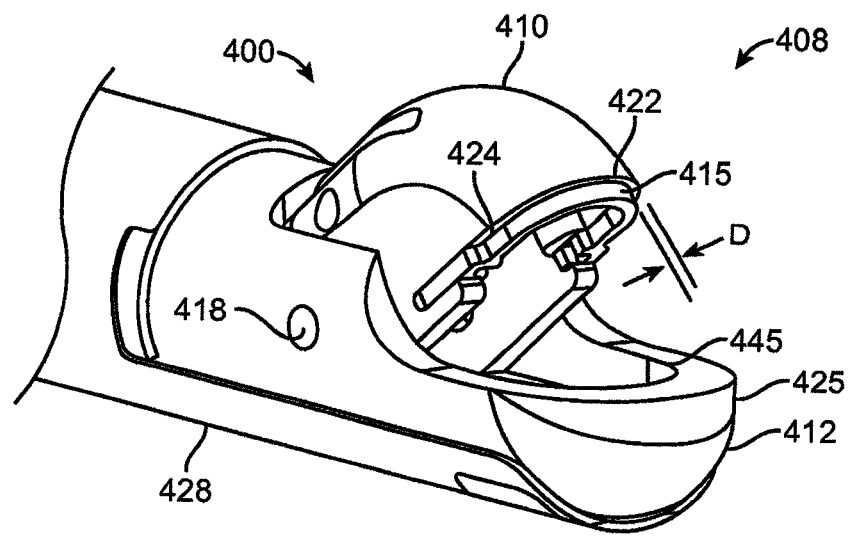
FIG. 9A is a perspective view of a working end of a probe with an electrosurgical jaw structure with the jaws in an open position.
Figure 9B:
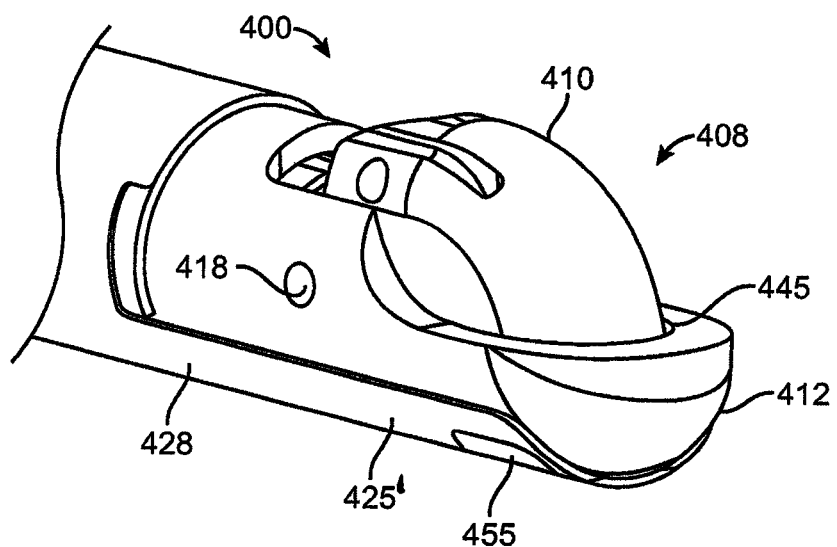
FIG. 9B is a view of the working end of the electrosurgical jaw structure of FIG. 9A with the jaws in a closed position.

FIGS. 9A-9B illustrate another working end 400 of a probe with a jaw structure 408 with first or upper jaw 410 and lower jaw 412. In this variation, the upper jaws 410 again has a cup shape and carries an active electrode 415 that extends in a U-shape around the perimeter of the upper jaw 410. The upper jaw 410 is formed of a dielectric material such as a ceramic with the electrode 415 secured thereto. The electrode is operatively coupled to an RF source 285 as shown in FIG. 2. The upper jaw 410 rotates around pivot pin 418 and can be actuated as the previous embodiment above. As can be seen in FIG. 9A, the electrode 415 can be set back from the outermost edge 422 of the jaw face 424 by a dimension D which can be from 0.05 mm to 2 mm, so that the lower jaw 412 can function as a return electrode 425. Alternatively, the lower jaw can comprise a ceramic material and the elongate outer sleeve 428 can function as a return electrode indicated at 425'. It can be understood from FIGS. 9A-9B that the cavity 440 in the jaws when closed allows the electrode 415 with a cutting current from RF source 285 to shear tissue chips from targeted tissue as the electrode 415 passes the edge 445 of the lower jaw 412. The targeted tissue is submerged in saline as in known in arthroscopic surgeries. The targeted tissue typically comprises at least one of cartilage, meniscus, connective tissue, tendons, and ligaments as in any arthroscopic procedure.

An electrosurgical probe as shown in FIGS. 9A-9B can connect RF current from RF source 285 through the handpiece 104 (FIG. 2) to the probe hub and jaw structure 408 as further described in co-pending U.S. patent applications Ser. No. 15/454,390 filed Mar. 9, 2017 (Atty. Docket No. 41879-716.201) and Ser. No. 15/454,432 filed Mar. 9, 2017 (Atty. Docket No. 41879-715.201) which are incorporated herein by this reference.

In the variation of FIGS. 9A-9B, the upper jaw 410 rotates on a pivot pin 418, but it should be appreciated that flex hinges or living hinges are also possible. In another variation, it should be appreciated that another electrode 455 (see FIG. 9B) can be disposed on an outer surface of the lower jaw 412, or either jaw surface, which can be configured for ablation or coagulation as is known in the art.

In another variation, a probe with a jaw opening and closing mechanism similar to that described above can operate a working end comprising a mechanical scissors or shears for cutting tissue.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An arthroscopic cutter, comprising:
a handpiece having a motor drive;
a shaft assembly having a working end and a hub end;
an openable-closeable jaw structure at the working end of the shaft assembly; and
a hub at the hub end of the shaft assembly;
wherein the hub is configured for detachable coupling to the handpiece;
wherein the motor drive is configured to couple to the jaw structure to open and close the jaw structure to cut tissue when the hub is coupled to the handpiece; and
wherein the openable-closeable jaw structure comprises a cup-shaped upper jaw having a U-shaped perimeter and a lower jaw having a U-shaped perimeter, said upper jaw being pivotally attached to the lower jaw, and said lower jaw being fixed to the working end of the shaft assembly, wherein the upper jaw can be reciprocated relative to the fixed lower jaw by the motor drive to cut tissue therebetween.

2. The arthroscopic cutter of claim 1 wherein the U-shaped perimeters of the upper and lower jaws of the jaw structure each have sharp edge portions configured for cutting tissue.

3. The arthroscopic cutter of claim 1 wherein the hub includes a gear mechanism configured to amplify an output torque of the motor drive to increase a closing force of the jaw structure.

4. The arthroscopic cutter of claim 3 wherein the gear mechanism increases the motor output torque by at least a factor of 10.

5. The arthroscopic cutter of claim 3 wherein the gear mechanism increases the motor output torque by at least a factor of 20.

6. The arthroscopic cutter of claim 3 wherein the gear mechanism increases the motor output torque by at least a factor of 40.

7. The arthroscopic cutter of claim 3 wherein the gear mechanism increases the motor output torque by at least a factor of 60.

8. The arthroscopic cutter of claim 3 wherein the gear mechanism increases the motor output torque to at least 10 in-lbs, 40 in-lbs, 60 in-lbs, or 80 in-lbs.

9. The arthroscopic cutter of claim 3 wherein the gear mechanism includes a planetary gear set.

10. The arthroscopic cutter of claim 3 further comprising a mechanism for converting a rotational motion of the motor drive to a linear motion to reciprocate an actuator member for opening and closing the jaw structure, wherein the gear mechanism is operatively coupled to the mechanism for converting the rotational motion.

11. The arthroscopic cutter of claim 1 wherein the motor drive is configured to open and close the jaw structure at a rate of at least 1 CPS (cycles per second).

12. The arthroscopic cutter of claim 1 wherein the motor drive is configured to open and close the jaw structure at a rate between 1 CPS and 100 CPS.

13. The arthroscopic cutter of claim 1 wherein the motor drive is configured to open and close the jaw structure at a rate between 1 CPS and 10 CPS.

14. The arthroscopic cutter of claim 1 further comprising a passageway extending through the shaft assembly to the working end, wherein said passageway is configured for connection to a negative pressure source.

15. The arthroscopic cutter of claim 14 wherein the handpiece includes an actuator for actuating the negative pressure source.

16. The arthroscopic cutter of claim 14 wherein the handpiece includes an actuator for actuating the motor drive and negative pressure source.

17. The arthroscopic cutter of claim 14 further comprising a processor configured to modulate the negative pressure source in response to actuation of the motor drive.

18. The arthroscopic cutter of claim 14 further comprising a processor configured to modulate the negative pressure source relative to a fully open position, partially open position or a closed position of the jaw structure.

19. The arthroscopic cutter of claim 1 further comprising a processor configured to control the motor drive to stop movement of the upper jaw relative to the lower jaw of the jaw structure in a selected default position.

20. The arthroscopic cutter of claim 19 further comprising a sensor in the handpiece configured to sense a magnet carried by a moving member coupled to the jaw structure to indicate the default position and non-default position.

21. The arthroscopic cutter of claim 20 wherein the default position is the jaw-open position.

22. The arthroscopic cutter of claim 20 wherein the default position the jaw-closed position.

23. The arthroscopic cutter of claim 1 wherein the handpiece includes an actuator for actuating the motor drive to open and close the jaw structure at a rate of at least 1 CPS (cycles per second).

24. The arthroscopic cutter of claim 1 wherein the handpiece includes an actuator for actuating the motor drive to move the jaw structure to a jaw-open position.

25. The arthroscopic cutter of claim 1 wherein the handpiece includes an actuator for actuating the motor drive to move the jaw structure to a jaw-closed position.

26. The arthroscopic cutter of claim 1 wherein the U-shaped perimeters of the upper and lower jaws of the jaw structure includes RF electrode edge portions configured for cutting tissue.

27. The arthroscopic cutter of claim 1 wherein each of the lower jaw and the upper jaw have an edge portion configured for shearing tissue.

28. The arthroscopic cutter of claim 1 wherein the lower jaw of the jaw structure has at least one a cup-shaped jaw geometry adapted for cutting and capturing tissue.

29. The arthroscopic cutter of claim 1 wherein at least one of the upper jaw or the lower jaw has a metal cutting edge.

30. The arthroscopic cutter of claim 1 wherein at least one of the upper jaw or the lower jaw includes a ceramic material.

31. The arthroscopic cutter of claim 1 wherein at least one of the upper jaw or the lower jaw has a ceramic cutting edge.

32. The arthroscopic cutter of claim 1 wherein the lower jaw of the jaw structure has a U-shaped slot therein which allows the cup-shaped upper jaw to pivot downwardly therethrough.

33. The arthroscopic cutter of claim 1 wherein the upper jaw pivots around a pivot point in a lower jaw housing.

34. The arthroscopic cutter of claim 33 wherein the upper jaw is reciprocated by an axial actuation rod which is attached to a location on the upper jaw that is offset from the pivot point.

\* \* \* \* \*